(12) United States Patent
Kawabata et al.

(10) Patent No.: US 11,317,843 B2
(45) Date of Patent: May 3, 2022

(54) BIOMAGNETISM MEASURING DEVICE

(71) Applicants: National University Corporation Tokyo Medical and Dental University, Tokyo (JP); TDK CORPORATION, Tokyo (JP)

(72) Inventors: Shigenori Kawabata, Tokyo (JP); Takato Fukui, Tokyo (JP); Tomohiko Shibuya, Tokyo (JP)

(73) Assignees: National University Corporation Tokyo Medical and Dental University, Tokyo (JP); TDK CORPORATION, Tokyo (JP)

( * ) Notice: Subject to any disclaimer, the term of this patent is extended or adjusted under 35 U.S.C. 154(b) by 596 days.

(21) Appl. No.: 16/321,852

(22) PCT Filed: Aug. 1, 2017

(86) PCT No.: PCT/JP2017/027794
§ 371 (c)(1),
(2) Date: Jan. 30, 2019

(87) PCT Pub. No.: WO2018/025829
PCT Pub. Date: Feb. 8, 2018

(65) Prior Publication Data
US 2019/0167136 A1     Jun. 6, 2019

(30) Foreign Application Priority Data
Aug. 2, 2016   (JP) .............................. JP2016-152306

(51) Int. Cl.
*A61B 5/242*   (2021.01)
*G01R 33/09*   (2006.01)
(Continued)

(52) U.S. Cl.
CPC ................ *A61B 5/242* (2021.01); *A61B 5/05* (2013.01); *A61B 5/6843* (2013.01); *G01R 33/02* (2013.01);
(Continued)

(58) Field of Classification Search
CPC .. A61B 5/04; A61B 5/25; A61B 5/251; A61B 5/05; A61B 5/0205; A61B 5/0816;
(Continued)

(56) References Cited

U.S. PATENT DOCUMENTS 3,758,854 A * 9/1973 Zimmerman ......... H01L 39/223
324/248
4,700,135 A * 10/1987 Hoenig ............... G01R 33/0358
324/248
(Continued)

FOREIGN PATENT DOCUMENTS

CN   102048541 A   5/2011
JP   H02-91508 U   7/1990
(Continued)

OTHER PUBLICATIONS

JPH0542120 (A) English Translation (Year: 1993).*
(Continued)

*Primary Examiner* — Oommen Jacob
(74) *Attorney, Agent, or Firm* — Osha Bergman Watanabe & Burton LLP

(57) ABSTRACT

The objective of the present invention is to provide a biomagnetism measuring device capable of accurately detecting biomagnetism regardless of the object to be measured. This biomagnetism measuring device (1) is provided with: a plurality of magnetic sensors (11) which detect biomagnetism of a living body (100); a retaining portion (12) including retaining holes (12*a*) which retain the plurality of magnetic sensors (11) with freedom to move
(Continued)

individually; and a movement mechanism which moves the magnetic sensors (11) individually in a contacting/separating direction causing the magnetic sensors (11) to come into contact with or separate from the living body (100). As movement mechanisms there may be mentioned, for example, a pneumatic/hydraulic mechanism (20), a resilient body mechanism (30), a screw mechanism (40) and a gear mechanism (50).

14 Claims, 10 Drawing Sheets

(51) Int. Cl.
| | | |
|---|---|---|
| *A61B 5/05* | (2021.01) | |
| *G01R 33/02* | (2006.01) | |
| *A61B 5/00* | (2006.01) | |
| *G01R 33/04* | (2006.01) | |
| *G01R 33/06* | (2006.01) | |

(52) U.S. Cl.
CPC ............ *G01R 33/09* (2013.01); *G01R 33/04* (2013.01); *G01R 33/063* (2013.01)

(58) Field of Classification Search
CPC .......... A61B 5/6843–6844; A61B 5/242–246; G01R 33/09; G01R 33/02; G01R 33/04; G01R 33/063
See application file for complete search history.

(56) References Cited

U.S. PATENT DOCUMENTS

| | | | | |
|---|---|---|---|---|
| 4,793,355 | A * | 12/1988 | Crum ................... | A61B 5/245 600/409 |
| 4,889,124 | A * | 12/1989 | Schneider ............. | A61B 5/242 600/409 |
| 5,408,178 | A * | 4/1995 | Wikswo, Jr. .......... | G01R 33/10 324/201 |
| 5,442,289 | A * | 8/1995 | Dilorio ................ | G01R 33/035 324/248 |
| 5,471,985 | A * | 12/1995 | Warden ................ | G01R 33/035 600/409 |
| 5,475,306 | A * | 12/1995 | Ludeke ............... | G01R 33/0354 324/248 |
| 5,494,033 | A * | 2/1996 | Buchanan .......... | G01R 33/0358 600/409 |
| 5,817,000 | A * | 10/1998 | Souder ................ | A61N 2/12 600/15 |
| 5,880,588 | A * | 3/1999 | Kado .................. | A61B 5/242 324/248 |
| 5,891,031 | A * | 4/1999 | Ohyu .................. | A61B 5/245 600/409 |
| 5,896,645 | A * | 4/1999 | Kado ................. | G01R 33/0354 29/602.1 |
| 6,230,037 | B1 * | 5/2001 | Tsukada ............. | G01R 33/0354 600/409 |
| 6,650,107 | B2 * | 11/2003 | Bakharev ........... | G01R 33/0354 324/202 |
| 7,047,059 | B2 * | 5/2006 | Avrin ................... | G01V 3/08 600/409 |
| 7,144,376 | B2 * | 12/2006 | Nakai .................. | A61B 6/5247 600/508 |
| 2002/0077537 | A1 * | 6/2002 | Avrin ................... | G01V 3/08 600/409 |
| 2003/0016010 | A1 * | 1/2003 | Kandori ............. | G01R 33/0356 324/248 |
| 2004/0254443 | A1 * | 12/2004 | Gott ................... | G01R 33/0354 600/409 |
| 2009/0012384 | A1 | 1/2009 | Adachi et al. | |
| 2009/0295385 | A1 * | 12/2009 | Brazdeikis ............ | A61B 5/704 324/309 |
| 2014/0062472 | A1 | 3/2014 | Nishikawa | |
| 2019/0167136 | A1 * | 6/2019 | Kawabata ............ | A61B 5/25 |

FOREIGN PATENT DOCUMENTS

| | | |
|---|---|---|
| JP | H05-42120 A | 2/1993 |
| JP | H08-98820 A | 4/1996 |
| JP | 2012-020143 A | 2/2012 |
| JP | 2012-095939 A | 5/2012 |
| JP | 5839527 B1 | 1/2016 |

OTHER PUBLICATIONS

International Search Report issued in PCT/JP2017/027794 dated Sep. 5, 2017 (2 pages).
Written Opinion of the International Searching Authority issued in PCT/JP2017/027794 dated Sep. 5, 2017 (4 pages).
Extended European Search Report issued in Application No. 17836934.4, dated Nov. 19, 2019 (8 pages).
Adachi et al.; "Biomagnetic Measurement System for Supine Subjects with Expanded Sensor Array and Real-time Noise Reduction;" 2015 37th Annual International Conference of the IEEE Engineering in Medicine and Biology Study (EMBC), IEEE; XP032811819 Aug. 25, 2015 (4 pages).
L. P. Ichkitidze et al. "Magnetic Field Sensors in Medical Diagnostics" Biomedical Engineering, vol. 48, No. 6; pp. 305-309; Mar. 1, 2015 (5 pages).
S. Tumanski "Modem magnetic field sensors—a review" Przeglad Elektrotechniczny, pp. 1-12; Oct. 1, 2013 (12 pages).
K. Hikaru et al. "Magnetocardiogram measured by fundamental mode orthogonal fluxgate array" Journal of Applied Physics, American Institute of Physics, vol. 117, No. 17; May 7, 2015 (3 pages).
S. Lau et al. "Optimal Magnetic Sensor Vests for Cardiac Source Imaging" Sensors, vol. 16, No. 6; May 24, 2016 (17 pages).
Office Action issued in European Application No. 17836934.4; dated Nov. 2, 2020 (8 pages).

* cited by examiner

BIOMAGNETISM MEASURING DEVICE

TECHNICAL FIELD

The present invention relates to a biomagnetism measuring device that uses magnetic sensors.

BACKGROUND ART

As a magnetic sensor that detects magnetism, there is conventionally known a magneto resistive (MR) sensor which uses a magneto resistive element (MR element). Direct current resistance acting on the MR element fluctuates according to the strength of the magnetic field. The MR sensor detects magnetic field variance or the presence of magnetic material as a change in voltage using the degree of fluctuation of the direct current resistance.

MR sensors are widely used as magnetic heads in hard disc devices, rotation sensors (encoders) and position sensors. Further, in recent years, the widespread use of mobile devices such as smartphones and tablet devices has led to such mobile devices being provided with an orientation sensor that has an MR sensor which uses geomagnetism to measure orientation. The information obtained from the orientation sensor is used for navigation or other purposes that use location information obtained by a global positioning system (GPS).

However, highly precise magnetic detection technology is not required for industrial applications. For example, in rotation sensors and position sensors, highly precise magnetic detection is not required because magnets and the like are used as reference signals. Further, orientation sensors do not require highly precise magnetic detection because they can achieve their function provided they can detect absolute orientation with geomagnetism as a reference.

Incidentally, for medical applications, biomagnetism measuring devices such as magnetoencephalographs, magnetocardiography and magnetomyographs which detect weak, low frequency magnetic fields generated by electrical activities in the brain, heart or muscles in a body have been used in recent years. Brain's magnetic fields generated by electrical activities in the brain are approximately 1/100 million the strength of the earth's magnetic field, and cardiac magnetic fields generated by electrical activities of the heart are approximately 1/1 million the strength of the earth's magnetic field. Because of this, the magnetic sensors used to detect magnetic fields generated by the body (hereinafter also referred to as "biomagnetism") are required to have the ability to perform extremely precise detection.

As a high-precision magnetic sensor that is capable of highly precise magnetic detection, there is known a superconducting quantum interference device (hereinafter also referred to as "SQUID") (see, for example, Patent Document 1).

A SQUID sensor is a magnetic sensor that uses the phenomenon of superconductivity and has a Josephson junction. Because of this, SQUID sensors need to be cooled with a refrigerant such as liquid helium or liquid nitrogen during use. Therefore, SQUID sensors must be provided in a dewar that stores refrigerant, which makes it difficult for SQUID sensors to make close contact with a body in order to detect biomagnetism.

Further, a plurality of the SQUID sensors are arranged in an array inside the dewar. However, the SQUID sensors must be arranged such that the Josephson junctions inside the SQUID sensors are not electromagnetically affected. Therefore, it is difficult to change the arrangement of SQUID sensors and replace or remove SQUID sensors.

Therefore, SQUID sensors have a problem in that, despite being high-precision magnetic sensors, they cannot be used close enough to the body and are difficult to handle.

In light of this, there has been proposed a biomagnetism measuring device that uses MR sensors which can detect slight magnetism at room temperature, thereby eliminating the need for cooling. For example, in Patent Document 2, there is proposed a biomagnetism measuring device in which a covering member that shields the body from an external magnetic field is formed into a helmet shape or a cylindrical shape, and MR sensors are provided inside the covering member in an array. With this biomagnetism measuring device that uses MR sensors, there is no need to dispose the MR sensors in a dewar. In addition, the MR sensors are easier to handle and can be brought closer to the body, compared to when using a device that uses SQUID sensors.

Patent Document 1: Japanese Unexamined Patent Application, Publication No. 2012-020143

Patent Document 2: Japanese Unexamined Patent Application, Publication No. 2012-095939

DISCLOSURE OF THE INVENTION

Problems to be Solved by the Invention

However, if the MR sensors are fixed in place as in the biomagnetism measuring device described in Patent Document 2, the MR sensors may not be able to detect magnetism depending on the subject to be measured (a body) because of a lack of close contact between the subject to be measured and the MR sensors. For example, optimal MR sensor positions will be different between adults and children and subjects to be measured that have a body shape different to that of a human, such as an animal. In addition, optimal positions of the MR sensors will differ depending on the site to be measured, such as position of the head, the heart and the positions of the four limbs of an animal.

It is an object of the present invention to provide a biomagnetism measuring device that can accurately detect biomagnetism regardless of the subject to be measured.

Means for Solving the Problems

The inventors of the present invention carried out extensive research in order to solve the above-mentioned problem. As a result, the inventors found that it is possible to provide a biomagnetism measuring device that can accurately detect biomagnetism regardless of the subject to be measured by retaining a plurality of magnetic sensors such that the magnetic sensors can move freely and move the magnetic sensors to optimal positions depending on the subject to be measured. Thus, the inventors completed the present invention. More specifically, the present invention provides the following.

(1) The present invention is a biomagnetism measuring device that includes a plurality of magnetic sensors that detect biomagnetism; a holding portion including holding holes that movably and separately hold the plurality of magnetic sensors; and a movement mechanism that moves the magnetic sensors in directions that approach and separate from a subject to be measured causing the magnetic sensors to come into contact with or separate from the subject to be measured.

(2) The present invention is the biomagnetism measuring device according to (1) in which the movement mechanism is at least one of a pneumatic mechanism, a hydraulic mechanism, a resilient body mechanism, a screw mechanism and a gear mechanism.

(3) The present invention is the biomagnetism measuring device according to (1) or (2) in which the movement mechanism is made of a nonmagnetic material.

(4) The present invention is the biomagnetism measuring device according to any one of (1) to (3), further including control means for controlling, on the basis of externally acquired biological information, movement of the magnetic sensors using the movement mechanism.

(5) The present invention is the biomagnetism measuring device according to any one of (1) to (4) in which the magnetic sensors further include contact detection means for detecting contact with the subject to be measured.

(6) The present invention is the biomagnetism measuring device according to any one of (1) to (5) in which the magnetic sensors further include biological information acquisition means for acquiring biological information.

(7) The present invention is the biomagnetism measuring device according to any one of (1) to (6) in which the magnetic sensors are disposed directly beneath the subject to be measured.

(8) The present invention is the biomagnetism measuring device according to any one of (1) to (7) in which the holding portion is made of a flexible material.

Effects of the Invention

According to the present invention, there can be provided a biomagnetism measuring device that can accurately detect biomagnetism regardless of the subject to be measured.

PREFERRED MODE FOR CARRYING OUT THE INVENTION

An embodiment of the present invention is described in detail below, but the present invention is not limited to the following embodiment and may be changed as appropriate without departing from the object of the present invention.
<Biomagnetism Measuring Device 1>

Figure 1:
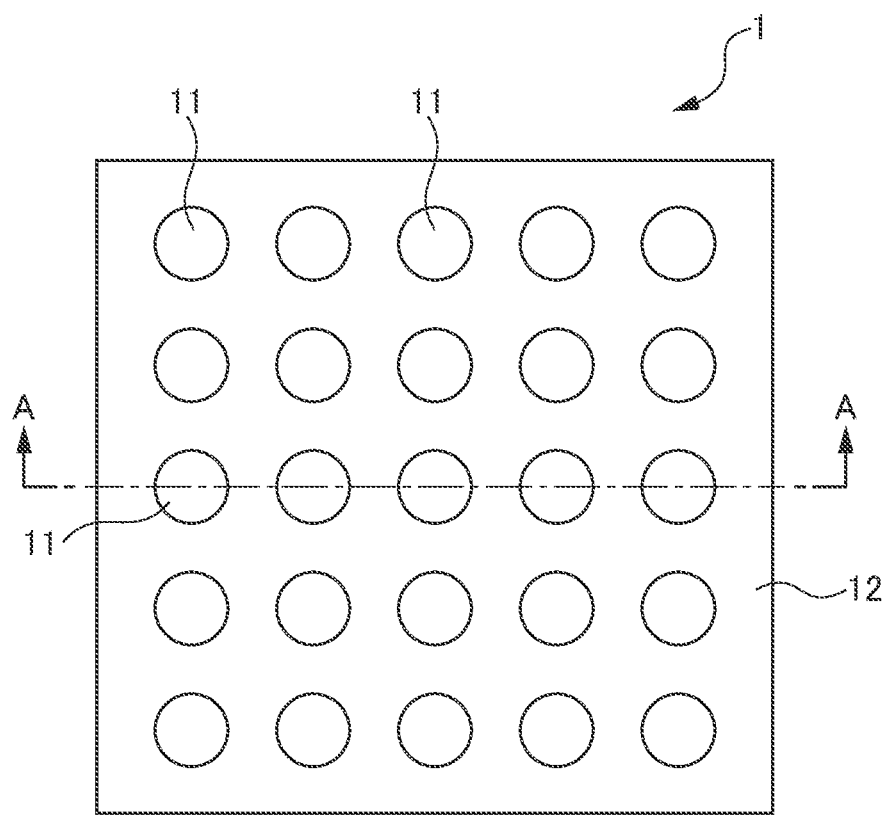
FIG. 1 is a plan view for illustrating an exemplary configuration of a biomagnetism measuring device according to an embodiment of the present invention.
Figure 2:
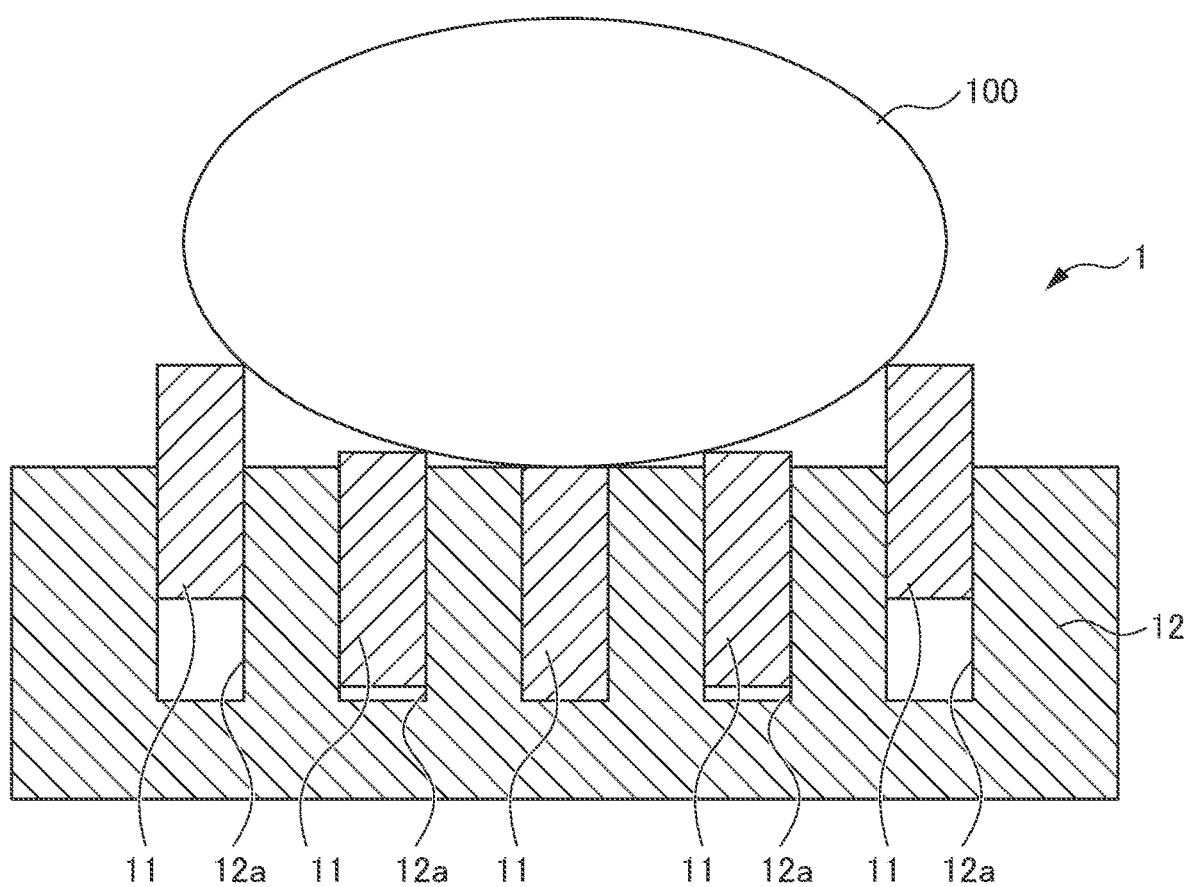
FIG. 2 is a schematic view for explaining the positional relationship between a subject and magnetic sensors of the biomagnetism measuring device.

FIG. 1 is a plan view for illustrating an example of a biomagnetism measuring device according to an embodiment of the present invention. FIG. 2 is a schematic view for explaining the positional relationship between a subject and magnetic sensors of the biomagnetism measuring device and is a cross-section taken along the line A-A' in the biomagnetism measuring device illustrated in FIG. 1. As illustrated in FIGS. 1 and 2, the biomagnetism measuring device 1 includes a plurality of magnetic sensors 11 that detect biomagnetism, a retaining portion 12 formed with retaining holes 12a that hold the magnetic sensors 11 such that the magnetic sensors 11 can move freely and a movement mechanism configured to move detection surfaces of the magnetic sensors 11 in directions that approach and separate from a living body (hereinafter also referred to as a "subject") 100 as a subject to be measured.

[Magnetic Sensor 11]

The magnetic sensors 11 are configured to detect biomagnetism generated by the living body 100 to be measured. Examples of the type of sensor used as the magnetic sensor 11 include a giant magnetoresistance sensor (GMR sensor), a tunnel magneto resistance sensor (TMR sensor), an anisotropic magneto resistive sensor (AMR sensor), magnetic impedance sensor (MI sensor) and a fluxgate sensor. The magnetic sensor 11 used in this embodiment may be any kind of magnetic sensor provided that the magnetic sensor can detect a magnetic field (normal component) between about $10^{-4}$ T (tesla) and $10^{-10}$ T (tesla). The magnetic sensor 11 used in this embodiment can acquire the same amount of information as a SQUID sensor, can be used at room temperature and does not need to be disposed in a dewar that stores refrigerant. In addition, the magnetic sensors 11 can be brought closer to the living body 100 and are easier to handle than when SQUID sensors are used.

The magnetic sensors 11 may or may not have wiring for giving/receiving signals and power supply. However, because the plurality of magnetic sensors 11 are disposed in the biomagnetism measuring device 1, the biomagnetism measuring device 1 preferably includes wiring as illustrated in FIG. 1 in order to prevent complex wiring.

Signals detected by the magnetic sensors 11 are sent to a control unit. The control unit generates biomagnetic information from the signals detected by the magnetic sensors 11 and visualizes and outputs this information to a display device.

[Retaining Portion 12]

The retaining portion 12 is formed with the retaining holes 12a that hold the plurality of magnetic sensors 11 such that the magnetic sensors 11 can individually move freely. The retaining holes 12a are arranged in an array. FIG. 1 shows an example where the retaining holes 12a are arranged in a 5×5 array. However, the number of retaining holes 12a (magnetic sensors 11) and the direction the retaining holes 12a are arranged in may be appropriately selected according to the subject to be measured and the measurement site.

The above-described retaining portion 12 is preferably made of a plastic material such as an acrylic resin, a nonferrous metal such as aluminum, titanium, copper, brass or specially processed stainless-steel alloy, or a nonmagnetic material such as wood. Forming the retaining portion 12 of a nonmagnetic material can suppress fluctuation in environmental magnetism even if the retaining portion 12 vibrates due to the subject 100 moving, for example, breathing. Therefore, the influence of fluctuation in environmental magnetism on the magnetic sensors 11 can be suppressed.

Figure 3:
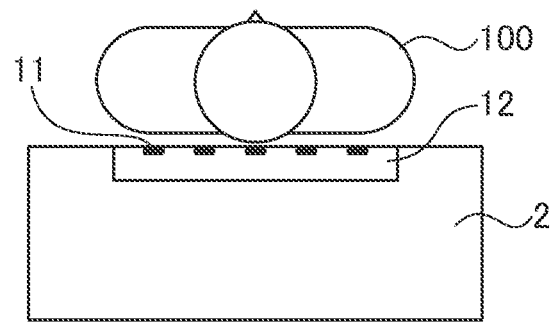
FIG. 3 is an explanatory diagram for explaining a configuration in which the magnetic sensors are disposed directly beneath the subject.
Figure 4:
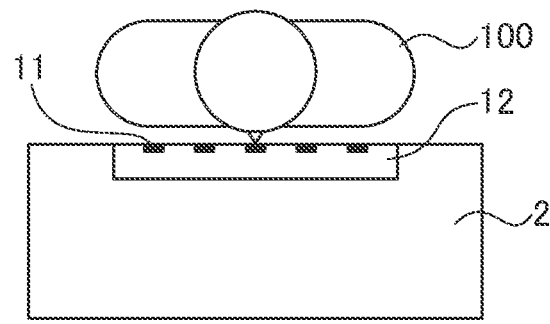
FIG. 4 is an explanatory diagram for explaining another configuration in which the magnetic sensors are disposed directly beneath the subject.

The retaining portion 12 is preferably placed directly beneath the subject to be measured so as to enhance contact between the detection surfaces of the magnetic sensors 11 and the subject to be measured. For example, as illustrated in FIG. 3, the subject 100 may lay face-up on an examination table 2 incorporated with the retaining portion 12. Alternatively, as illustrated in FIG. 4, the subject 100 may lay face-down on the examination table 2. Through the subject 100 laying down on the examination table 2 incorporated with the retaining portion 12, gravity works on the subject 100 to improve contact between the body surface of the subject 100 and the detection surfaces of the magnetic sensors 11. As a result, the biomagnetism measuring device 1 can obtain more accurate biomagnetic information.

[Movement Mechanisms]

The movement mechanisms separately move the magnetic sensors 11 in a contact or separation direction to cause the magnetic sensors 11 to come into contact with or separate from the living body 100, to thereby cause close contact between the detection surfaces of the magnetic sensors 11 and the living body 100 as the subject to be measured. The movement mechanisms are not particularly limited provided that the movement mechanisms can move the magnetic sensors 11 to a predetermined position. Examples of the movement mechanisms include a pneumatic mechanism, a hydraulic mechanism, a resilient body mechanism, a screw mechanism and a gear mechanism.

(Pneumatic/Hydraulic Mechanism 20)

Figure 5:
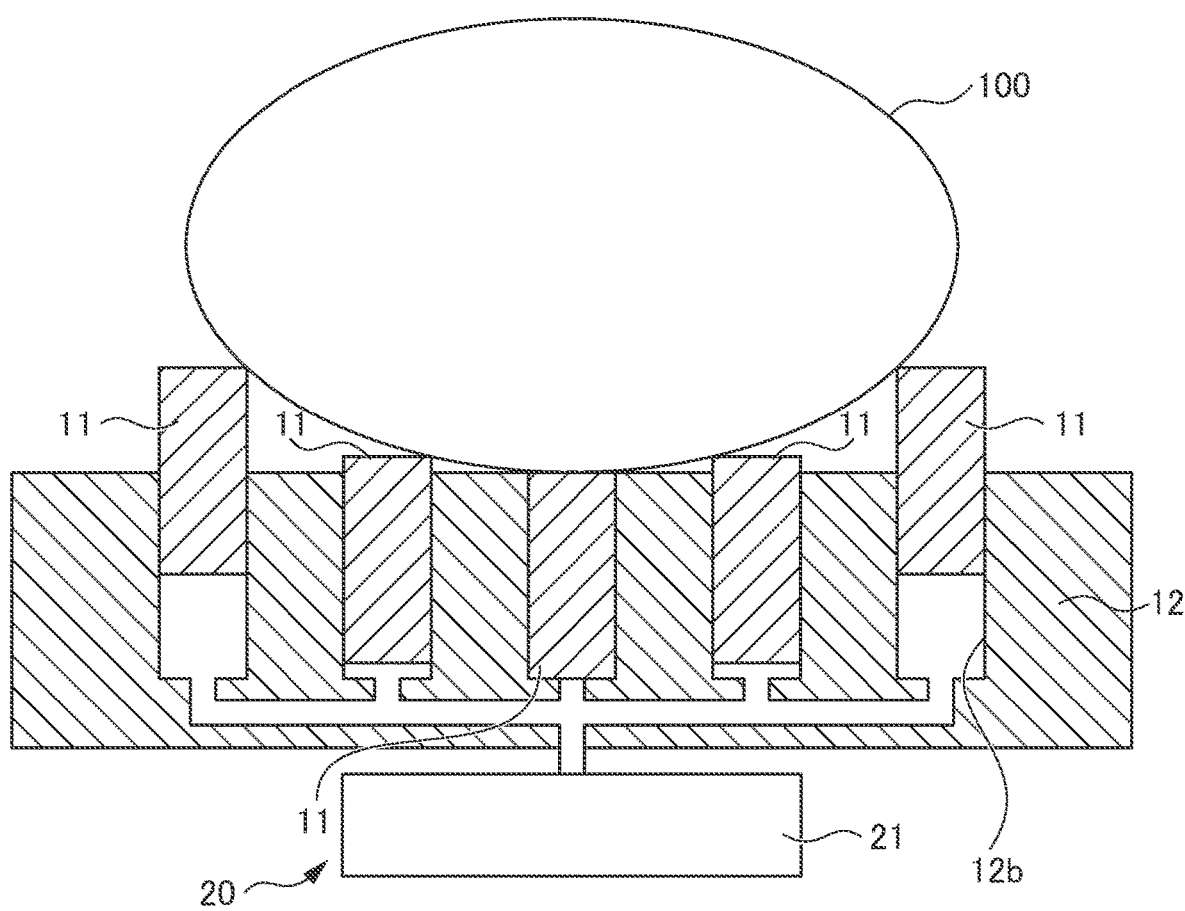
FIG. 5 is a schematic diagram for illustrating an example of a biomagnetism measuring device that includes a pneumatic/hydraulic mechanism.

FIG. 5 is a schematic diagram for illustrating an example of a biomagnetism measuring device that includes a pneumatic/hydraulic mechanism. In FIG. 5, components that are the same as those in FIGS. 1 and 2 are denoted by the same reference symbols and a description thereof is omitted. As illustrated in FIG. 5, a pneumatic/hydraulic mechanism 20 increases/reduces pneumatic pressure or hydraulic pressure in the retaining holes 12b using a pump 21 to move the detection surfaces of the magnetic sensors 11 in the retaining holes 12b in a direction approaching the subject to be measured or in a direction separating from the subject to be measured. The pneumatic/hydraulic mechanism 20 uses air or oil that does not affect the sensitivity of the magnetic sensors 11.

(Resilient Body Mechanism 30)

Figure 6:
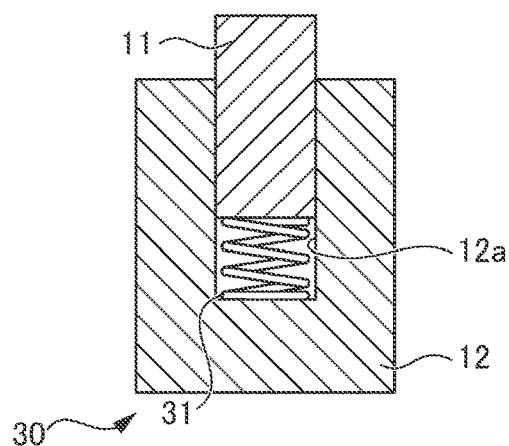
FIG. 6 is an expanded schematic diagram of a main portion for illustrating an example of a biomagnetism measuring device that includes a resilient body mechanism.

FIG. 6 is an expanded schematic diagram of a main portion for illustrating an example of a biomagnetism measuring device that includes a resilient body mechanism. In FIG. 6, components that are the same as those in FIGS. 1 and 2 are denoted by the same reference symbols and a description thereof is omitted. As illustrated in FIG. 6, in a resilient body mechanism 30, a resilient body member 31 such as a coil screw is provided in each retaining hole 12a. Repulsive force generated by the subject to be measured increases or reduces the expansion/contraction of the resilient body member 31 to achieve close contact between the subject to be measured and the detection surfaces of the magnetic sensors 11 in the retaining holes 12a. The resilient body mechanism 30 has a simple configuration that does not require a drive source.

(Screw Mechanism 40)

Figure 7:
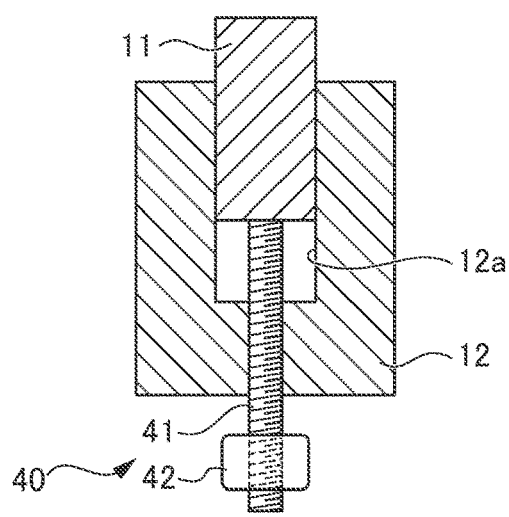
FIG. 7 is an expanded schematic diagram of a main portion for illustrating an example of a biomagnetism measuring device that includes a screw mechanism.

FIG. 7 is an expanded schematic diagram of a main portion for illustrating an example of a biomagnetism measuring device that includes a screw mechanism. In FIG. 7, components that are the same as those in FIGS. 1 and 2 are denoted by the same reference symbols and a description thereof is omitted. As illustrated in FIG. 7, a screw mechanism 40 includes a screw shaft 41 and a screw nut 42 to which the screw shaft 41 is screwed in. A drive motor (not shown) rotationally drives the screw nut 42 to increase/reduce rotation of the screw shaft 41 to move the detection surface of the magnetic sensor 11 in the retaining hole 12a in a direction approaching the subject to be measured or in a direction separating from the subject to be measured. As described later, in the screw mechanism 40, a control unit increases/reduces rotation of the screw shaft 41 to allow the magnetic sensors 11 to be separately moved to a predetermined position.

(Gear Mechanism 50)

Figure 8:
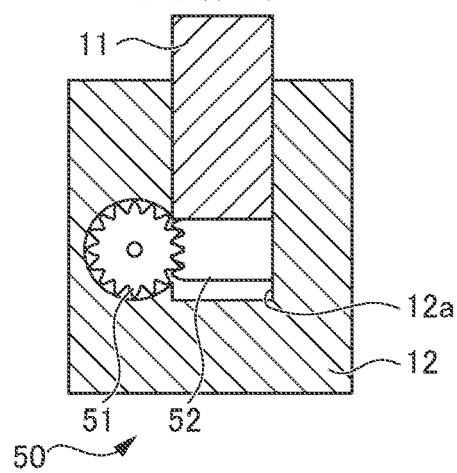
FIG. 8 is an expanded schematic diagram of a main portion for illustrating an example of a biomagnetism measuring device that includes a gear mechanism.

FIG. 8 is an expanded schematic diagram of a main portion for illustrating an example of a biomagnetism measuring device that includes a gear mechanism. In FIG. 8, components that are the same as those in FIGS. 1 and 2 are denoted by the same reference symbols and a description thereof is omitted. As illustrated in FIG. 8, a gear mechanism 50 includes a gear 51 and a meshing portion 52 that meshes with the gear 51. A drive motor (not shown) rotationally drives the gear 51 to increase/reduce movement of the meshing portion 52 and move the magnetic sensor 11 in the retaining hole 12a. The gear 51 may be configured of a plurality of gears. As described later, in the gear mechanism 50, a control unit increases/decreases movement of the meshing portion 52 to allow the magnetic sensors 11 to be separately moved to a predetermined position.

The above-described movement mechanisms such as the resilient body mechanism 30, the screw mechanism 40 and the gear mechanism 50 are preferably made of a plastic material such as an acrylic resin, a nonferrous metal such as aluminum, titanium, copper, brass or a specially processed stainless-steel alloy, or a nonmagnetic material such as wood. Even if the members move due to operation of the movement mechanism, fluctuations in environmental magnetism can be suppressed because the members are made of a nonmagnetic material. Therefore, influence of fluctuations in environmental magnetism on the magnetic sensors 11 can be suppressed.

[Control Unit]

In the biomagnetism measuring device 1 according to the present embodiment, the movement of each magnetic sensor 11 caused by the movement mechanism may be controlled by a control unit. For example, the control unit may control the movement mechanism such as the pneumatic/hydraulic mechanism 20, the screw mechanism 40 and the gear mechanism 50 on the basis of externally acquired biological information to adjust the movement of each magnetic sensor 11.

Figure 9:
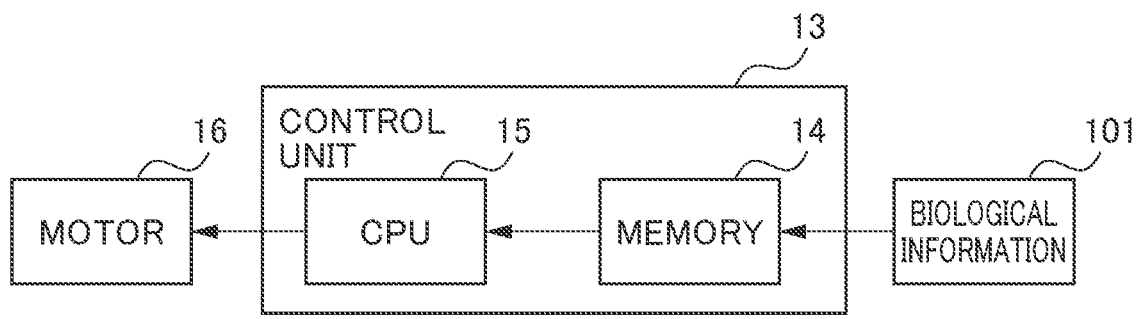
FIG. 9 is a block diagram for illustrating the configuration of the biomagnetism measuring device.

FIG. 9 is a block diagram for illustrating a configuration of the biomagnetism measuring device including a control unit that determines movement on the basis of externally acquired biological information. For example, as illustrated in FIG. 9, a control unit 13 of the biomagnetism measuring device 1 may store previously acquired biological information 101 in a memory 14 and use a central processing unit (CPU) 15 to calculate the number of revolutions of a plurality of drive motors 16 provided in the movement mechanisms on the basis of the stored biological information 101. Then, the control unit 13 may control the movement of each magnetic sensor 11. As a result, the biomagnetism measuring device 1 can move each magnetic sensor 11 to an appropriate position on the basis of the biological information 101. The externally acquired biological information 101 is, for example, information on a biological cross-section of the body type of the subject 100 obtained by MRI measurement.

[Modification Example of Magnetic Sensor]

The magnetic sensors 11 may further include detection means for detecting information other than magnetic information on the living body 100. Examples of such detection means include contact detection means that detects contact between the magnetic sensor 11 and the living body 100 and biological information acquisition means that acquires information on the living body 100.

(Magnetic Sensor Including Contact Detection Means)

Figure 10:
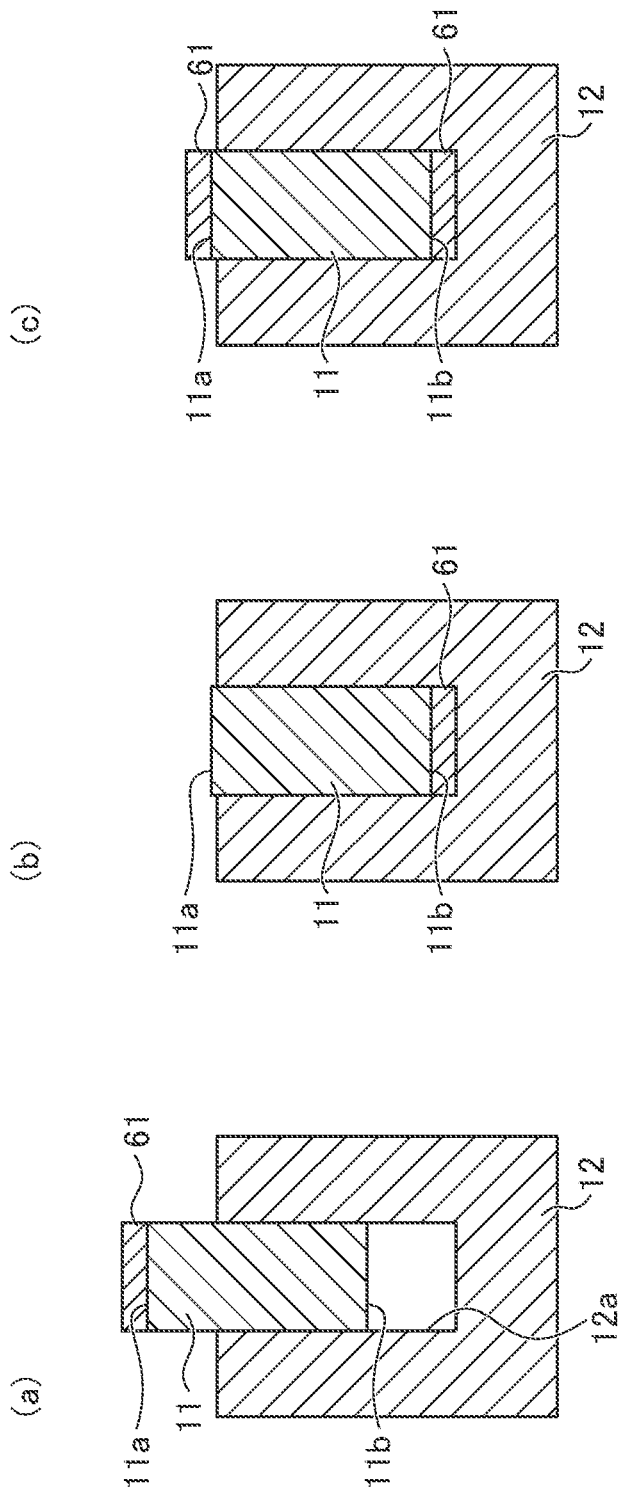
FIGS. 10(a), (b) and (c) are expanded schematic diagrams of a main portion for illustrating an exemplary configuration in which the magnetic sensor includes a pressure sensor.

The magnetic sensor 11 may include a pressure sensor or a position sensor as the contact detection means for detecting contact with the living body 100. FIGS. 10(*a*), (*b*) and (*c*) are expanded schematic diagrams of a main portion for illustrating an exemplary configuration in which the magnetic sensor includes a pressure sensor that detects contact with a body. For example, as illustrated in FIG. 10(*a*), the magnetic sensor 11 may include, on a detection surface 11*a* that opposes the subject to be measured, a pressure sensor 61 that detects contact with the living body 100. Alternatively, as illustrated in FIG. 10(*b*), the magnetic sensor 11 may include the pressure sensor 61 on a surface 11*b* that opposes the detection surface 11*a* of the magnetic sensor. Alternatively, as illustrated in FIG. 10(*c*), the magnetic sensor 11 may include pressure sensors 61 on both the detection surface 11*a* of the magnetic sensor 11 and the surface 11*b* that opposes the detection surface 11*a*. The pressure sensor 61 disposed on the surface 11*b* that opposes the detection surface 11*a* of the magnetic sensor 11 detects stress. This stress is a combination of stress from the subject to be measured and stress from the movement mechanism. Then, the control unit 13 determines whether the magnetic sensor 11 and the living body 100 are in contact with each other on the basis of detection results from the pressure sensor 61.

Figure 11:
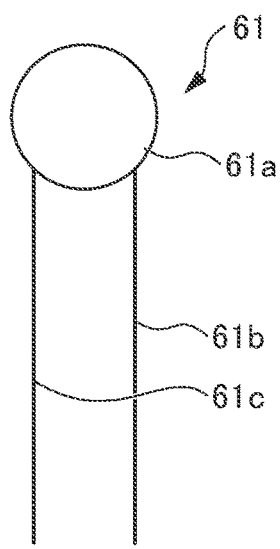
FIG. 11 is a schematic diagram for illustrating a configuration of the pressure sensor.

The pressure sensor 61 may be any sensor provided that the pressure sensor 61 outputs a pressure signal according to the applied pressure to the control unit 13. For example, as illustrated in FIG. 11, the pressure sensor 61 measures pressure from the subject to be measured using a pressure-sensitive element through a diaphragm 61*a*, converts the pressure into an electrical signal and sends this electrical signal to the control unit 13 via two connection cables 61*b* and 61*c*.

With the control unit 13, contact between the magnetic sensor 11 and the living body 100 can be determined on the basis of the electrical signal output from the pressure sensor 61 or the position sensor. The control unit 13 may be configured not to give and receive signals or supply power between magnetic sensors 11 that are not in contact with the subject to be measured, to thereby save power. In addition, the control unit 13 can select only information from magnetic sensors 11 that are in contact with the subject to be measured and generate biomagnetic information.

(Magnetic Sensor Including Biological Information Acquisition Means)

Figure 12:
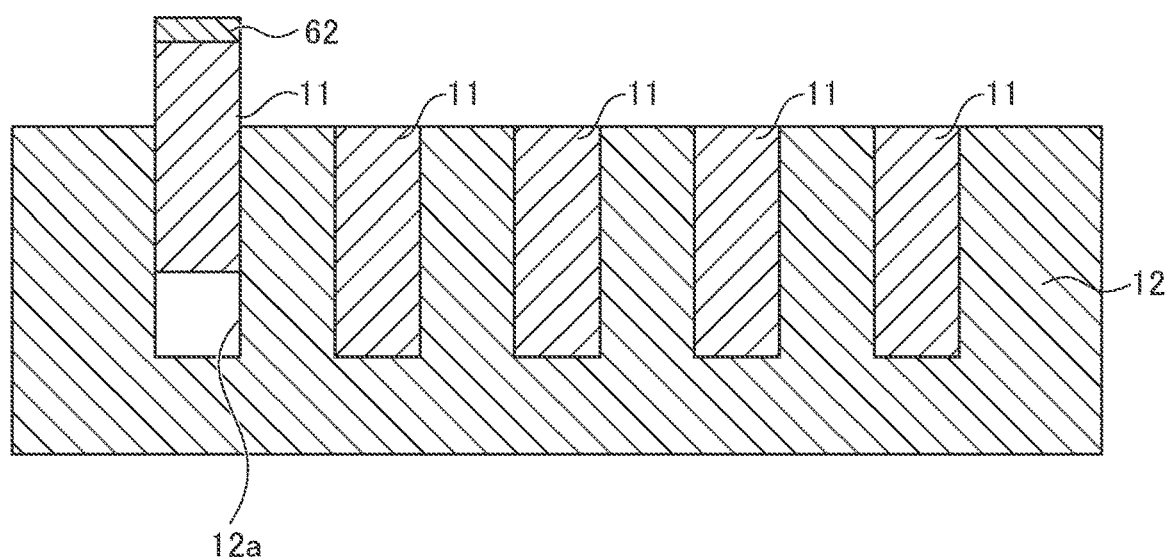
FIG. 12 is a schematic diagram for illustrating an exemplary configuration in which the magnetic sensor includes detection means for detecting biological information.
Figure 13:
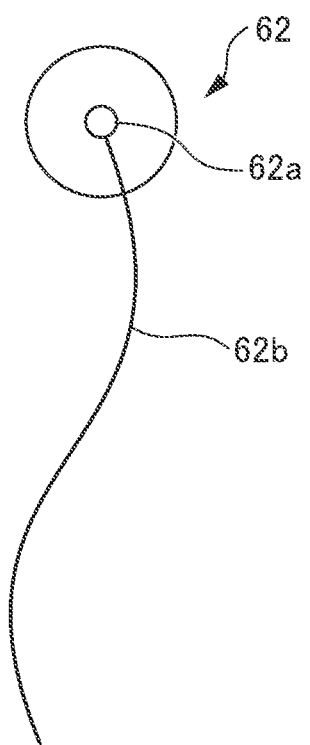
FIG. 13 is a schematic diagram for illustrating a configuration of a bioelectrode.

In addition, the magnetic sensor 11 may include a bioelectrode or a pressure sensor as biological information acquisition means for acquiring biomagnetic information. FIG. 12 is a schematic diagram for illustrating an exemplary configuration in which the magnetic sensor includes detection means for detecting biological information. As illustrated in FIG. 12, the magnetic sensor 11 may include a bioelectrode 62 as biological information acquisition means on a detection surface that opposes the subject to be measured. For example, as illustrated in FIG. 13, the bioelectrode 62 includes an electrode portion 62*a* and biological information acquired by the electrode portion 62*a* is sent to the control unit 13 via the connection cable 62*b*. Examples of the biological information acquired by the bioelectrode 62 or the pressure sensor includes an electrocardiogram, heart rate, pulse, number of breaths or muscle potential.

With the control unit 13, biological information other than biomagnetic information can be acquired and the biological information can be visualized and output to a display device. Therefore, the person conducting the measurement can circumstantially acquire a plurality of types of information in one measurement with one biomagnetism measuring device.

[Modification Example of Retaining Portion]

Figure 14:
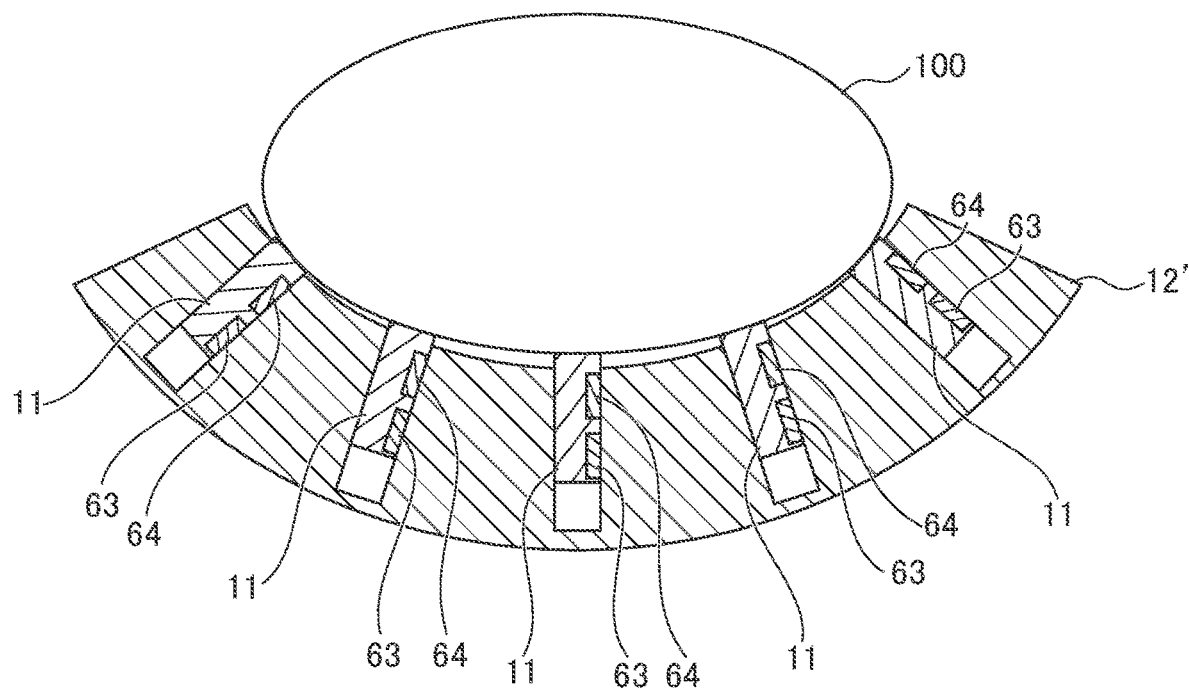
FIG. 14 is a schematic diagram for illustrating an example of a biomagnetism measuring device in which the retaining portion is made of a flexible material.

The retaining portion 12 illustrated in FIG. 2 is made of a rigid material, but the retaining portion may be made of a flexible material. FIG. 14 is a schematic diagram for illustrating an example of a biomagnetism measuring device in which the retaining portion is made of a flexible material. As illustrated in FIG. 14, a retaining portion 12' is made of a flexible material. Therefore, even if the subject to be measured has a curved or uneven surface, the retaining portion 12' deforms to fit the shape of the subject to be measured. Because of this, the magnetic sensors 11 held by the retaining portion 12' can achieve increased contact area between the detection surfaces and the subject to be measured and biomagnetism can be detected more accurately.

In addition, as illustrated in FIG. 14, the magnetic sensors 11 in the retaining portion 12' may include a position sensor 63 that detects the position of the magnetic sensor 11 or an angle sensor 64 that detects the inclination of the magnetic sensor 11. With the control unit 13, a relative position between the magnetic sensor 11 and the subject to be measured may be calculated on the basis of the results of detection by the position sensor 63 or the angle sensor 64 and magnetic distribution of biomagnetism or the currents source may be estimated using this information. In addition, the control unit 13 may visualize the detection results and display and output the results to a display device.

The flexible material used for the retaining portion 12' may be a resilient material such as natural rubber or synthetic rubber, or a synthetic resin such as polypropylene, polyethylene, acrylic, polycarbonate, vinyl chloride and polyethylene terephthalate (PET). The entire retaining portion 12' does not need to be made of a flexible material. For example, a plurality of fixing portions that respectively fix the retaining holes may be made of a rigid material and the fixing portions may be linked to each other with hinges made of a flexible material.

EXPLANATION OF REFERENCE NUMERALS 1 biomagnetism measuring device
2 examination table 11 magnetic sensor
12 retaining portion
12a, 12b retaining hole
13 control unit
14 memory
15 CPU
20 pneumatic/hydraulic mechanism
21 pump
30 resilient body mechanism
31 resilient body member
40 screw mechanism
41 screw shaft
42 screw nut
50 gear mechanism
51 gear
52 meshing portion
61 pressure sensor
62 bioelectrode
63 position sensor
64 angle sensor
100 living body (subject)
101 biological information

The invention claimed is:

1. A biomagnetism measuring device comprising:
a plurality of magnetic sensors that have detection surfaces and detect magnetism of a living body as a subject to be measured;
a retaining portion including retaining holes that hold the plurality of magnetic sensors such that the magnetic sensors can individually move freely; and
a movement mechanism that is at least one of a pneumatic mechanism, a hydraulic mechanism, a resilient body mechanism, a screw mechanism, and a gear mechanism and moves the magnetic sensors in directions that approach and separate from the subject to be measured causing the magnetic sensors to come into contact with or separate from the subject to be measured,
wherein the magnetic sensors are giant magnetoresistance sensors (GMR sensors), tunnel magneto resistance sensors (TMR sensors), anisotropic magneto resistive sensors (AMR sensors), magnetic impedance sensors (MI sensors), or fluxgate sensors, and
wherein the detection surfaces of the magnetic sensors are provided at vertically upper ends of the magnetic sensors to oppose the subject to be measured and to allow gravity working on the subject to improve contact between the subject and the detection surfaces of the magnetic sensors.

2. The biomagnetism measuring device according to claim 1, wherein some part of the movement mechanism is made of a nonmagnetic material.

3. The biomagnetism measuring device according to claim 1, further comprising control means for controlling, on the basis of externally acquired biological information, movement of the magnetic sensors using the movement mechanism.

4. The biomagnetism measuring device according to claim 1, wherein the magnetic sensors further include contact detection means for detecting contact with the subject to be measured.

5. The biomagnetism measuring device according to claim 1, wherein the magnetic sensors further include biological information acquisition means for acquiring biological information.

6. The biomagnetism measuring device according to claim 1, wherein the magnetic sensors are disposed directly beneath the subject to be measured.

7. The biomagnetism measuring device according to claim 1, wherein some part of the retaining portion is made of a flexible material.

8. The biomagnetism measuring device according to claim 2, further comprising control means for controlling, on the basis of externally acquired biological information, movement of the magnetic sensors using the movement mechanism.

9. The biomagnetism measuring device according to claim 2, wherein the magnetic sensors further include contact detection means for detecting contact with the subject to be measured.

10. The biomagnetism measuring device according to claim 3, wherein the magnetic sensors further include contact detection means for detecting contact with the subject to be measured.

11. The biomagnetism measuring device according to claim 2, wherein the magnetic sensors further include biological information acquisition means for acquiring biological information.

12. The biomagnetism measuring device according to claim 3, wherein the magnetic sensors further include biological information acquisition means for acquiring biological information.

13. The biomagnetism measuring device according to claim 4, wherein the magnetic sensors further include biological information acquisition means for acquiring biological information.

14. The biomagnetism measuring device according to claim 2, wherein the magnetic sensors are disposed directly beneath the subject to be measured.

* * * * *